US010130707B2

(12) United States Patent
Gunther et al.

(10) Patent No.: US 10,130,707 B2
(45) Date of Patent: Nov. 20, 2018

(54) TOPICAL PHARMACEUTICAL COMPOSITION BASED ON SEMIFLUORINATED ALKANES (75) Inventors: Bernhard Gunther, Dossenheim (DE); Bastian Theisinger, Mannheim (DE); Sonja Theisinger, Mannheim (DE); Dieter Scherer, Laufen (CH)

(73) Assignee: NOVALIQ GMBH, Heidelberg (DE)

( * ) Notice: Subject to any disclaimer, the term of this patent is extended or adjusted under 35 U.S.C. 154(b) by 72 days.

(21) Appl. No.: 14/122,044

(22) PCT Filed: May 24, 2012

(86) PCT No.: PCT/EP2012/059787
§ 371 (c)(1),
(2), (4) Date: Nov. 25, 2013

(87) PCT Pub. No.: WO2012/160179
PCT Pub. Date: Nov. 29, 2012

(65) Prior Publication Data
US 2014/0100180 A1 Apr. 10, 2014

(30) Foreign Application Priority Data

May 25, 2011 (EP) .................................. 11167552
May 26, 2011 (EP) .................................. 11167732

(51) Int. Cl.
| | | |
|---|---|---|
| A01N 43/00 | (2006.01) |
| A01N 43/46 | (2006.01) |
| A61K 31/55 | (2006.01) |
| A61K 45/06 | (2006.01) |
| A61K 9/00 | (2006.01) |
| A61K 9/107 | (2006.01) |
| A61K 47/06 | (2006.01) |
| A61K 31/436 | (2006.01) |
| A61K 9/08 | (2006.01) |
| A61K 31/355 | (2006.01) |

(52) U.S. Cl.
CPC ............ *A61K 45/06* (2013.01); *A61K 9/0014* (2013.01); *A61K 9/08* (2013.01); *A61K 9/1075* (2013.01); *A61K 31/355* (2013.01); *A61K 31/436* (2013.01); *A61K 47/06* (2013.01)

(58) Field of Classification Search
CPC ......... A01N 43/00; A01N 43/46; A61K 31/55
USPC ....................................................... 514/217
See application file for complete search history.

(56) References Cited

U.S. PATENT DOCUMENTS

| 10,022 A | 9/1853 | Stockwell |
| 2,616,927 A | 11/1952 | Kauck et al. |
| 5,077,036 A | 12/1991 | Long, Jr. |
| 5,326,566 A | 7/1994 | Parab |
| 5,336,175 A | 8/1994 | Mames |
| 5,518,731 A | 5/1996 | Meadows |
| 5,667,809 A | 9/1997 | Trevino et al. |
| 5,874,469 A | 2/1999 | Maniar et al. |
| 5,874,481 A | 2/1999 | Weers |
| 5,981,607 A | 11/1999 | Ding et al. |
| 6,042,845 A | 3/2000 | Sun et al. |
| 6,113,919 A | 9/2000 | Reiss et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,372,243 B2 | 4/2002 | Kobuch |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz et al. |
| 7,001,607 B1 | 2/2006 | Menz et al. |
| 7,026,359 B1 | 4/2006 | Gross |
| 7,258,869 B1 | 8/2007 | Berry et al. |
| 7,740,875 B2 | 6/2010 | Dechow |
| 8,029,977 B2 | 10/2011 | Meinert et al. |
| 8,470,873 B2 | 6/2013 | Chen |
| 8,614,178 B2 | 12/2013 | Theisinger et al. |
| 8,986,738 B2 | 3/2015 | Meinert |
| 9,241,900 B2 | 1/2016 | Wilson |
| 9,308,262 B2 | 4/2016 | Gunther et al. |
| 2002/0128527 A1 | 9/2002 | Meinert |
| 2003/0018044 A1 | 1/2003 | Peyman |
| 2003/0027833 A1 | 2/2003 | Cleary et al. |
| 2004/0265362 A1 | 12/2004 | Susilo |
| 2004/0266702 A1 | 12/2004 | Dawson et al. |
| 2005/0079210 A1 | 4/2005 | Gupta |
| 2005/0175541 A1 | 8/2005 | Lanza et al. |
| 2006/0153905 A1 | 7/2006 | Carrara et al. |
| 2008/0207537 A1* | 8/2008 | Turner et al. ................... 514/31 |
| 2008/0260656 A1 | 10/2008 | Mallard |
| 2009/0226875 A1* | 9/2009 | Meinert et al. ................ 435/1.1 |
| 2010/0008996 A1 | 1/2010 | Meinert |
| 2010/0226997 A1 | 9/2010 | Bowman et al. |
| 2010/0274215 A1 | 10/2010 | Wong et al. |
| 2011/0269704 A1 | 11/2011 | Seigfried |

(Continued)

FOREIGN PATENT DOCUMENTS

| EP | 0 670 159 A1 | 9/1995 |
| EP | 0 965 329 A1 | 12/1999 |

(Continued)

OTHER PUBLICATIONS

Ahmed, I. et al., "Disposition of Timolol and Inulin in the Rabbit Eye Following Corneal Versus Non-Corneal Absorption," International Journal of Pharmaceutics, 1987, 38, 9-21.

(Continued)

*Primary Examiner* — Layla Soroush
(74) *Attorney, Agent, or Firm* — Hoxie & Associates LLC (57) ABSTRACT

The invention provides liquid or semi-solid pharmaceutical compositions for topical administration comprising a semifluorinated alkane. The compositions are useful for the delivery of active ingredients into the deep layers of the skin or skin appendages. Various active ingredients may be incorporated, such as immunosuppressants, antiinfectives, antifungal agents, antiinflammatory agents, and retinoids.

19 Claims, 3 Drawing Sheets

(56) References Cited

U.S. PATENT DOCUMENTS

| | | |
|---|---|---|
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0140942 A1 | 5/2014 | Günther et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0101178 A1 | 4/2016 | Wilson |
| 2016/0159902 A1 | 6/2016 | Gunther et al. |
| 2017/0087100 A1 | 3/2017 | Scherer et al. |
| 2017/0087101 A1 | 3/2017 | Scherer et al. |
| 2017/0143832 A1 | 5/2017 | Gunther et al. |

FOREIGN PATENT DOCUMENTS

| | | |
|---|---|---|
| EP | 0 965 334 A1 | 12/1999 |
| EP | 0 939 655 B1 | 6/2002 |
| EP | 1 152 749 B1 | 4/2006 |
| EP | 2 110 126 A1 | 10/2009 |
| EP | 2 332 525 A1 | 6/2011 |
| EP | 2 335 735 A1 | 6/2011 |
| EP | 2 462 921 A1 | 6/2012 |
| JP | S6452722 | 2/1989 |
| JP | 2000511157 A | 8/2000 |
| JP | 2001/158734 | 6/2001 |
| JP | 2008/518891 | 6/2008 |
| JP | 2011/006348 | 1/2011 |
| WO | WO 96/40052 A1 | 12/1996 |
| WO | WO 97/12852 A1 | 4/1997 |
| WO | WO 00/10531 | 3/2000 |
| WO | WO 00/24376 A1 | 5/2000 |
| WO | WO 00/54588 A1 | 9/2000 |
| WO | WO 02/49631 A1 | 6/2002 |
| WO | WO 2005/018530 | 3/2005 |
| WO | WO 2005/099718 A1 | 10/2005 |
| WO | WO 2005/099752 | 10/2005 |
| WO | WO 2005/123035 A1 | 12/2005 |
| WO | WO 2006/007510 A1 | 1/2006 |
| WO | WO 2006/042059 | 4/2006 |
| WO | WO 2006/048242 | 5/2006 |
| WO | WO 2007/052288 A2 | 5/2007 |
| WO | WO 2008/060359 A2 | 5/2008 |
| WO | WO 2010/062394 A2 | 6/2010 |
| WO | WO 2010/146536 | 12/2010 |
| WO | WO 2011/009436 | 1/2011 |
| WO | WO 2011/073134 A1 | 6/2011 |
| WO | WO 2012/052418 A1 | 4/2012 |
| WO | WO 2012/062834 A1 | 5/2012 |
| WO | WO 2012/093113 A1 | 7/2012 |
| WO | WO 2012/121754 | 9/2012 |
| WO | WO 2012/160180 A2 | 11/2012 |
| WO | WO 2013/110621 A2 | 8/2013 |
| WO | WO 2014/041055 A1 | 3/2014 |
| WO | WO 2014/041071 A1 | 3/2014 |
| WO | WO 2015/011199 | 1/2015 |

OTHER PUBLICATIONS

Chemical Book, 5-Fluorouracil, available at <http://www.chemicalbook.com/ChemicalProductProperty_EN_CB8162744.htm>, accessed Mar. 7, 2014, 1 page.

Davies, N., "Biopharmaceutical Considerations in Topical Ocular Drug Delivery," Clinical and Experimental Pharmacology and Physiology, 2000, 27, 558-562.

Dembinski, R. et al., "Semi-fluorinated Alkanes as Carriers for Drug Targeting in Acute Respiratory Failure," Experimental Lung Research, 2010, 36, 499-507.

Elkeeb, R. et al., "Transungual Drug Delivery: Current Status," International Journal of Pharmaceutics, 2010, 384, 1-8.

Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.

Griffin, W., "Classification of Surface-Active Agents by 'HLB'," Journal of the Society of Cosmetic Chemists, 1949, 1, 311-326.

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf [retrieved on Oct. 10, 2011].

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

International Preliminary Report on Patentability for International Application No. PCT/EP2011/068141 dated Apr. 23, 2013, 4 pages.

International Preliminary Report on Patentability for International Application No. PCT/EP2011/069795 dated May 14, 2013, 8 pages.

International Preliminary Report on Patentability for International Application No. PCT/EP2012/050043 dated Jul. 10, 2013, 5 pages.

International Preliminary Report on Patentability for International Application No. PCT/EP2012/059787 dated Nov. 26, 2013, 9 pages.

International Preliminary Report on Patentability for International Application No. PCT/EP2012/059788 dated Nov. 26, 2013, 8 pages.

International Search Report for International Application No. PCT/EP2011/068141 dated Dec. 14, 2011, 2 pages.

International Search Report for International Application No. PCT/EP2011/069795 dated Jan. 16, 2012, 3 pages.

International Search Report for International Application No. PCT/EP2012/050043 dated Apr. 24, 2012, 2 pages.

International Search Report for International Application No. PCT/EP2012/059787 dated Dec. 5, 2012, 4 pages.

International Search Report for International Application No. PCT/EP2012/059788 dated Dec. 3, 2012, 4 pages.

Meinert, H. et al., "The Use of Semifluorinated Alkanes in Blood-Substitutes," Biomaterials, Artificial Cells, and Immobilization Biotechnology, 1993, 21 (5), 583-595.

Meinert, H. et al., "Semifluorinated Alkanes—A New Class of Compounds with Outstanding Properties for Use in Ophthalmology," European Journal of Ophthalmology, 2000, 10 (3), 189-197.

Murdan, S., "Enhancing the Nail Permeability of Topically Applied Drugs," Expert Opinion on Drug Delivery, 2008, 5 (11), 1267-1282.

Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, abstract only.

Rosca-Casian, O. et al., "Antifungal Activity of *Aloe vera* Leaves," Fitoterapia, 2007, 28, 219-222.

Wong, D. et al., "Perfluorocarbons and Semifluorinated Alkanes," Seminars in Ophthalmology, 2000, 15 (1), 25-35.

U.S. Appl. No. 14/373,877, filed Jul. 22, 2014, Gunther et al.

Gayton, J., "Etiology, Prevalence, and Treatment of Dry Eye Disease," Clinical Ophthalmology, 2009, 3, 405-412.

International Preliminary Report on Patentability for International Application No. PCT/EP2013/051163 dated Jul. 29, 2014, 7 pages.

International Search Report for International Application No. PCT/EP2013/051163 dated Mar. 4, 2013, 4 pages.

Knepp, V., "Stability of Nonaqueous Suspension Formulations of Plasma Derived Factor IX and Recombinant Human Alpha Interferon at Elevated Temperatures," Pharmaceutical Research, 1998, 15 (7), 1090-1095.

Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.

Lemp, M., "Management of Dry Eye Disease," The American Journal of Managed Care, 2008, 14 (3), S88-S101.

Mackiewicz, J. et al., "In Vivo Retinal Tolerance of Various Heavy Silicone Oils," Investigative Ophthalmology & Visual Science, 2007, 48 (4), 1873-1883.

Perry, H., "Dry Eye Disease: Pathophysiology, Classification, and Diagnosis," The American Journal of Managed Care, 2008, 14 (3), S79-S87.

(56) References Cited

OTHER PUBLICATIONS

Rosenberg, A., "Effects of Protein Aggregates: An Immunologic Perspective," The AAPS Journal, 2006, 8 (3), E501-E507.
Stevenson, C., "Characterization of Protein and Peptide Stability and Solubility in Non-Aqueous Solvents," Current Pharmaceutical Biotechnology, 2000, 1, 165-182.
Wang, W., "Lyophilization and Development of Solid Protein Pharmaceuticals," International Journal of Pharmaceutics, 2000, 203, 1-60.
U.S. Appl. No. 14/427,927, filed Mar. 12, 2015, Günther et al.
U.S. Appl. No. 14/427,969, filed Mar. 12, 2015, Günther et al.
Baerdemaeker, L. et al., "Pharmacokinetics in Obese Patients," Continuing Education in Anaesthesia, Critical Care & Pain, 2004, 4, 152-155.
Broniatowski, M. et al., "Langmuir Monolayers Characteristic of (Perfluorodecyl)-Alkanes," Journal of Physical Chemistry B, 2004, 108, 13403-13411.
English-language machine translation of EP0670159 (A1) issued in U.S. Appl. No. 14/122,025 on Apr. 1, 2015, 10 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
Plassmann, M. et al., "Trace Analytical Methods for Semifluorinated n-Alkanes in Snow, Soil, and Air," Analytical Chemistry, 2010, 82(11), 4551-4557.
Plassmann, M. et al., "Theoretical and Experimental Simulation of the Fate of Semifluorinated n-Alkanes During Snowmelt," Environmental Science & Technology, 2010, 44 (17), 6692-6697.
Ujiie et al., "Successful Treamtent of Nail Lichen Planus with Topical Tacrolimus", Department of Dermatology, Hokkaido University Graduate School of Medicine, Nov. 4, 2009.
Zakeri et al., "Topical calcipotriol therapy in nail psoriasis", A study of 24 cases, Dermatology Online Journal, 11(3):5; 2005.
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed Feb. 10, 2016.
Barata-Vallejo et al., "(Me3Si)3SiH-Mediated Intermolecular Radical Perfluoroalkylation Reactions of Olefins in Water," J. Org. Chem., 2010, 75:6141-6148.
Bardin et al., "Long-Range Nanometer-Scale Organization of Semifluorinated Alkane Monolayers at the Air/Water Interface," Langmuir, 2011, 27:13497-13505.
Mantle et al., "Adverse and beneficial effects of plant extracts on skin and skin disorders," Adverse Drug Reaction and Toxicological Reviews, 2001, 20(2): 89-103.
Thomas et al., "The therapeutic uses of topical vitamin A acid," Journal of the American Academy of Dermatology, 1981, 4(5): 505-513.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Zhang et al., "Surface micelles of semifluorinated alkanes in Langmuir-Blodgett monolayers," Phys. Chem. Chem. Phys., 2004, 6:1566-1569.
Costa Gomes et al., "Solubility of dioxygen in seven fluorinated liquids," Journal of Fluorine Chemistry, 2004, 125:1325-1329.
Dias et al., "Solubility of oxygen in liquid perfluorocarbons," Fluid Phase Equilibria, 2004, 222-223:325-330.
Gerdenitsch, "Emulsions—established and promising drug carriers for parenteral administration," retrieved from Internet, date accessed: Jun. 20, 2016, URL: <http:/ipimediaworld.com/wp-content/uploads/2012/05/Pages-from-IPI-Volume-2-Issue-1-11.pdf.>.
Holm, R. et al., "A novel excipient, 1-perfluorohexyloctane shows limited utility for the oral delivery of poorly water-soluble drugs," European Journal of Pharmaceutical Sciences, 2011, 42:416-422.
International Preliminary Report on Patentability dated Sep. 18, 2012, for International Patent Application PCT/EP2011/053949, 9 Pages.
International Preliminary Report on Patentability dated Jan. 26, 2016, for International Application No. PCT/EP2014/065840, 11 pages.
International Search Report for International Application No. PCT/EP2011/053949 dated Sep. 6, 2011, 5 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages (English Machine Translation).

\* cited by examiner

TOPICAL PHARMACEUTICAL COMPOSITION BASED ON SEMIFLUORINATED ALKANES

CROSS REFERENCE TO RELATED APPLICATIONS

This application is the National Stage Entry under 35 U.S.C. § 371 of International Application No. PCT/EP2012/059787 filed May 24, 2012, which claims priority to European Patent Application No. 11167552.6 filed May 25, 2011, and European Patent Application No. 11167732.4 filed May 26, 2011, the contents of each of which are incorporated herein by reference.

BACKGROUND OF THE INVENTION

The present invention is in the field of pharmacotherapy. More specifically, it relates to the treatment of diseases and conditions affecting the skin and skin appendages.

The pharmacological treatment of cutaneous disorders may involve systemic or local administration of an effective medicament. Typically, whenever local (e.g. epicutaneous) administration is possible and leads to the desired outcome, it is preferred over systemic therapy which is, quite plausibly, more often associated with adverse systemic effects. However, effective treatment via the topical route of administration requires that the drug substance is soluble in, and/or otherwise compatible with a suitable carrier or vehicle, and that it reaches its target tissue layer(s) in an effective amount or concentration. In fact, in some cases, effective epicutaneous treatment is particularly difficult to achieve.

The skin consists of three main layers—the epidermis, the dermis and the hypodermis. The epidermis comprises the stratum corneum (the outermost superficial layer of skin, consisting of dead cells) and the vital (living) epidermis. Depending on the cutaneous disease or condition, one or more layers of the skin may become affected. In some dermatological conditions, such as ichthyosis, callus, or plaque psoriasis, the stratum corneum is thicker than in the healthy state and can provide a significantly greater barrier to the penetration of a therapeutical compound, thus reducing its efficacy in the treatment of the deeper layers of the skin. Moreover, it has been shown recently that with increasing age, the skin of a human also becomes more resistant to the penetration by drug substances.

The use of penetration enhancers has been proposed in order to achieve a sufficient and consistent availability of various therapeutic compounds at the site of action during the treatment of cutaneous diseases. For example, U.S. Pat. No. 5,326,566 describes a composition of a pharmacological agent in combination with dibutyl adipate, or a mixture of dibutyl adipate and isopropyl myristate, which could enhance the penetration through the skin and even increase the amount absorbed into the systemic circulation, if that is desired.

Even though a variety of penetration enhancers have been used for enhancing the absorption of therapeutic agents into and through the skin, substantial problems may arise when the penetration enhancers are incompatible with a particular drug substance, leading to drug instability and degradation into potentially harmful degradants.

US 2005/0079210 A1 proposes the use of liposomes the epicutaneous administration of drugs and cosmetically useful agents. However, liposomes are difficult to manufacture cost-effectively and in a reproducible manner.

Other novel formulation strategies for topical medications require the occlusion of the skin after administration, which is however perceived as inconvenient by many patients EP0670159A1 discloses stable oily emulsions comprising surfactant and semifluorinated alkane, which are proposed to be suitable for transporting oxygen to the skin or vascular system or for use as a standard for blood-gas analysis. The use of these compositions as carriers of active agent was also suggested, although no mention is made of whether these compositions are capable of effectively delivering active agents in particular to the deeper layers of the skin.

There clearly remains a need for pharmaceutical formulations and vehicles which allow the effective treatment of cutaneous disorders by topical administration. It is therefore an object of the present invention to provide such improved compositions which overcome one or more disadvantages of known compositions. In particular, it is an object of the invention to provide compositions of topically active drug substances which are effective and convenient. Further objects of the invention will become clear on the basis of the description of the invention below, including the examples, and of the patent claims.

SUMMARY OF THE INVENTION

The present invention provides a novel pharmaceutical composition for administration to the skin or a skin appendage. The composition comprises an effective amount of an active ingredient and a semifluorinated alkane (SFA) according to formula RFRH or RFRHRF, wherein RF is a perfluorinated hydrocarbon segment with 20 or less carbon atoms and RH is a non-fluorinated hydrocarbon segment with 3 to 20 carbon atoms. In a preferred embodiment, the SFA is selected from F4H5, F4H6, F4H8, F6H6 and F6H8.

It has been surprisingly found by the inventors that SFAs are capable of delivering active pharmaceutical ingredients effectively into the deeper layers of the skin, i.e. into the vital layers below the stratum corneum of the epidermis. Moreover, they are capable of delivering active ingredients deep into nails.

The composition may, for example, be in the form of a solution or an emulsion. They are useful for administering a wide range of topical agents indicated in a number of cutaneous diseases and conditions.

DETAILED DESCRIPTION OF THE INVENTION

The invention provides a novel pharmaceutical composition for use as a topical formulation which is to be administered to the skin or a skin appendage. The composition comprises an effective amount of an active ingredient and a semifluorinated alkane according to formula RFRH or RFRHRF, wherein RF is a perfluorinated hydrocarbon segment with 20 or less carbon atoms and RH is a non-fluorinated hydrocarbon segment with 3 to 20 carbon atoms, and in particular, wherein the perfluorinated segment is linear and comprises from 4 to 12 carbon atoms, and/or the non-fluorinated segment is linear and comprises from 4 to 8 carbon atoms.

The invention is based on the surprising discovery that the semifluorinated alkanes (SFAs) as defined above are highly suitable carriers for topically administered drugs and capable of delivering such drugs very effectively to the layers of the skin below the stratum corneum, i.e. the viable epidermis, but also to the dermis and hypodermis. This was particularly unexpected in view of Hardung (Doctoral Thesis, Albert-Ludwigs-University of Freiburg, Germany, 2008), who investigated the suitability of SFAs as carriers for topical medications using e.g. testosterone as a model drug, and who came to the conclusion that an SFA such as F6H8 (see below for an explanation of the terminology of SFAs) does not affect an improved penetration into the skin, interact with the stratum corneum or exhibit any penetration-enhancing effect (p. 103, first full paragraph). However, in spite of such discouraging statements in the prior art, the inventors have further investigated the impact of SFAs and SFA-based carriers on the delivery of drugs into the deeper layers of the skin and nails using excised human skin (in contrast to Hardung who used pig skin), and have now surprisingly found that SFAs are indeed capable of enhancing the penetration of drugs into the relevant skin layers, as will be shown in more detail below.

As used herein, a pharmaceutical composition is any composition comprising an active ingredient useful for the diagnosis, prevention, management or therapy of a disease, symptom or health condition and at least one carrier or excipient. A topical formulation is a composition which is in a form suitable for topical administration. In the present invention, the composition is suitable for administration to the skin or a skin appendage of a subject, which subject may be a human or an animal. The skin may be intact skin or injured, bruised, damaged or otherwise affected skin. A skin appendage is a structure derived from the skin, and usually adjacent to it, such as a hair, a sweat or sebaceous gland. Semifluorinated alkanes are linear or branched alkanes some of whose hydrogen atoms have been replaced by fluorine. In a preferred embodiment, the semifluorinated alkanes (SFA's) used in the present invention are composed of at least one non-fluorinated hydrocarbon segment and at least one perfluorinated hydrocarbon segment. Particularly useful are SFA's which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFA's having two or three segments as RFRH and RFRHRF, respectively, wherein $R_F$ designates a perfluorated hydrocarbon segment, $R_H$ designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFAs which are useful in the context of the present invention are also described in EP-A 965 334, EP-A 965329 and EP-A 2110126, the disclosure of which documents is incorporated herein.

In a further embodiment, the semifluorinated alkane is a compound according to the formula RFRH, whose segments $R_F$ and $R_H$ are linear and each—but independently from one another—have from 3 to 20 carbon atoms. In particular, the perfluorinated segment is linear and comprises from 4 to 12 carbon atoms, and/or the non-fluorinated segment is linear and comprises from 4 to 8 carbon atoms. Preferred SFA's include in particular the compounds F4H5, F4H6, F4H8, F6H4, F6H6, F6H8, and F6H10. Presently most preferred for carrying out the invention are F4H5, F4H6, F6H6 and F6H8.

Optionally, the composition may comprise more than one SFA. It may be useful to combine SFA's, for example, in order to achieve a particular target property such as a certain density, viscosity, or solubilising capacity for a particular active ingredient. If a mixture of SFA's is used, it is furthermore preferred that the mixture comprises at least one of F4H5, F4H6, F4H8, F6H4, F6H6, F6H8, and F6H10, and in particular one of F4H5, F4H6, F4H8, F6H6 and F6H8. In another embodiment, the mixture comprises at least two members selected from F4H5, F4H6, F4H8, F6H4, F6H6, F6H8, and F6H10, and in particular at least two members selected from F4H5, F6H6, F4H8, and F6H8. Furthermore, mixtures of a semifluorinated alkane, e.g. F4H5, with a perfluorinated compound, such as perfluorooctylbromide or perfluorodecalin, or with another oily material are also contemplated. Other oily materials would, for example, include silicone oils, triglycerides (e.g. native or synthetic medium-chain triglycerides), or compounds such as isopropyl myristate. In some preferred embodiments, however, perfluorinated compounds are absent.

Liquid SFA's are chemically and physiologically inert, colourless and stable. Their typical densities range from 1.1 to 1.7 g/cm$^3$, and their surface tension may be as low as 19 mN/m. SFA's of the RFRH type are insoluble in water but also somewhat amphiphilic, with increasing lipophilicity correlating with an increasing size of the non-fluorinated segment. Again, for practising the current invention, an SFA having a density of at least 1.2 g/cm$^3$ should be selected.

Liquid SFA's of the RFRH type are being used commercially for unfolding and reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds. On the other hand, SFA's have not been used as excipients in approved drug products as of today.

For allowing convenient administration to the skin or skin appendages, the composition is preferably liquid or semi-solid. As used herein, semi-solid means that a material behaves like a solid upon the exertion of low shear force, but above a certain force threshold, the so-called "yield point", it behaves like a viscous fluid. Whether liquid or semi-solid, the composition may represent a single phase (i.e. a solution), or consist of two or more phases.

In a particular embodiment, for example, the composition is in the form of an emulsion. As used herein, an emulsion is a system comprising a dispersed (or inner, or emulsified, or discontinuous) liquid phase within a continuous (or outer, or coherent) liquid or semisolid phase. The two phases are not miscible. In an O/W-emulsion (also referred to as oil-in-water emulsion), a water-immiscible organic liquid phase, which does not have to be an "oil" by any specific definition, is dispersed in a water-miscible continuous phase which may or may not be substantially comprised of water itself. Within emulsions, O/W-emulsions are preferred for carrying out the invention.

In another embodiment, the composition is in the form of a microemulsion. A microemulsion is a clear, thermodynamically stable, optically isotropic mixture of a lipophilic component, a hydrophilic component, and an amphiphilic component. Typically, a microemulsion forms spontaneously when the components are combined and mixed with each other, without requiring high energy input as is normally required for the formation of an "ordinary" emulsion. Microemulsions may have a colloidal lipophilic phase dispersed in a hydrophilic phase, or a hydrophilic phase colloidally dispersed in a lipophilic phase. The size of the dispersed phases is usually in the range from about 5 nm to about 400 nm, and most often below about 200 nm. In one of the preferred embodiments of the invention, the particle size is from about 5 nm to about 100 nm. In terms of its rheological properties, the microemulsion may be in the form of a liquid or a gel, i.e. in liquid or semisolid form. In a preferred embodiment, the microemulsion is in liquid form.

For microemulsions according to the invention, it is preferred to use an oil phase comprising from about 5 to about 95 wt.-% of SFA, and more preferably from about 10 to about 80 wt.-% of SFA, the remainder of the oil phase being another oil such as isopropylmyristate. With respect to the incorporation of aqueous components, surfactants and optionally cosurfactants, commonly known constituents of microemulsions may be used to formulate the composition.

The composition, whether formulated as a solution, microemulsion or conventional emulsion, may contain any further pharmaceutically acceptable ingredients as required or useful in view of the intended application. In a particular embodiment, an additional solvent or co-solvent may be incorporated, for example in order to achieve a higher solubility for a specific active ingredient, to modify the viscosity or stability of the formulation, or to further enhance the cutaneous penetration of the active ingredient. Such co-solvent should of course be selected in type, quality and amount such as to maintain the physiological tolerability of the formulation. Potentially suitable co-solvents include ethanol, acetone, ethyl acetate, isopropyl alcohol, glycerol, propylene glycol, pentylene glycol, polyethylene glycol, liquid paraffin, triglyceride oils, hydrofluorocarbons such as HFA 134a and/or HFA 227, and liquid mono- or diglycerides. Among these, ethanol and pentylene glycol are among the particularly preferred solvents. It has been found that relatively small amounts of ethanol may substantially modify the solubilising properties of SFAs and allow the incorporation of a number of active ingredients at higher concentrations. For example, the composition may comprise up to about 10 wt.-% of ethanol, or up to about 5 wt.-% of ethanol. Even at a low concentration of up to about 3 wt.-%, ethanol may be a very useful additive in the composition, depending on the specific drug substance to be delivered. Pentylene glycol is also very useful as co-solvent in general and, in particular, it has been found that its incorporation is advantageous in the formulation of microemulsions.

Moreover, the composition may comprise one or more stabilisers, surfactants (in particular if the composition is in the form of an emulsion or microemulsion), cosurfactants (in particular if it is in the form of a microemulsion), colouring agents, antioxidants (for example, α-tocopherol), thickeners (viscosity-increasing agents such as bentonite), and fragrances.

If a surfactant is present, it may, for example, be selected from physiologically acceptable phospholipids (such as phosphatidylcholines); nonionic surfactants such as fatty alcohols, pegylated glycerides, pegylated fatty acids, pegylated fatty alcohols, pegylated sorbitan fatty acid esters, and poloxamers; anionic surfactants such as sodium lauryl sulphate, docusate sodium, and sodium deoxycholate.

The composition may be prepared by commonly known techniques for the manufacture of pharmaceutical solutions, emulsions, and microemulsions. Depending on their consistency and specific use, they may be presented in bottles, spray bottles, or tubes.

The active ingredient incorporated within the composition may, in principle, be selected from drug substances which are useful for the prevention, management, or therapy of a cutaneous disease or condition.

In one of the specific embodiments, the active ingredient is poorly water-soluble. In particular, it water solubility is not more than about 1 mg/mL. In other preferred embodiments, the water solubility is not higher than about 0.1 mg/mL, or not more than about 10 μg/mL, respectively. The invention is particularly useful for delivering such active ingredients because it allows the administration of effective doses in relatively small volumes, which is at least partly due to the surprisingly high solubilisation capacity of semifluorinated alkanes for many poorly water-soluble drug substances.

For the avoidance of doubt, it is affirmed that the invention is not restricted to poorly water-soluble drug substances. It has been found that certain bioactive agents have substantial aqueous solubility, but can also be advantageously formulated in SFA-based carriers.

The active ingredient may be selected from drug substances useful for the prevention and in particular for the management and therapy of cutaneous diseases and conditions, such as psoriasis, dermatitis, erythema, acne, actinic keratosis, verrucae, and rosacea. The invention appears generally useful for delivering drug substances of various therapeutic categories to the deep layers of the skin, i.e. to the vital epidermis, the dermis, and/or to the hypodermis which may also be understood as being part of the integumentary system. Topical administration of the compositions to the skin may result in the delivery of the drug substance to the stratum corneum, as well as penetration through the strateum corneum and delivery of the active drug substance to these deeper skin layers. Cutaneous diseases or conditions may affect the stratum corneum, as well as one or more of the deeper skin layers. The composition may thus be used for the prevention or treatment of diseases or conditions that affect also the vital epidermis, the dermis and/or the hypodermis. In one of the specific embodiments, the composition is used in the therapy of psoriasis, and incorporates an active ingredient which may be used to control psoriasis or a symptom thereof. Such active ingredient may, for example, be an immunosuppressant drug, such as a macrolide immunosuppressant. Examples of potentially suitable macrolide immunosuppressants include tacrolimus, sirolimus, everolimus, tacrolimus, pimecrolimus, ridaforolimus, temsirolimus, zotarolimus, and ciclosporin A; or retinoids such as retinol, retinal, tretinoin, isotretinoin, alitretinoin, etretinate, acitretin, tazarotene, bexarotene and adapalene. Tacrolimus is one of the particularly preferred drugs in this group. It has been found by the inventors that tacrolimus can be very effectively (i.e. faster and deeper than using conventional formulations) delivered to the deep and viable layers of the skin using the composition of the invention (see Example 1).

As illustrated in Example 1, the composition of the invention may be used to effectively deliver an active ingredient such as a macrolide immunosuppressant, as for example tacrolimus, to the deeper layers of the skin. For example, at least about 5% of the topically administered amount of drug may be delivered to the vital epidermis within only about 30 minutes. The composition may also be used to deliver at least 5% of the topically administered drug to the dermis within about 30 minutes, or even at least about 10% of the administered dose. Also in terms of delivery to the hypodermis, the composition may be used to deliver at least 5% of the topically administered amount of drug to this layer within the same period of time, or even 10% or more.

Taking into account the typical thickness of the respective skin layers, the composition may be used to deliver within about 30 minutes at least about 15% of the topically administered drug dose to a depth of at least about 10 µm. In other embodiments, at least about 20% of the dose is delivered to a depth of at least about 10 µm. The composition may also be used to deliver at least about 10% of the topically administered drug to a depth of 100 µm or more within about 30 minutes; or at least about 15% or at least about 20% of the dose, respectively.

Another therapeutic indication in which it is of great importance that the therapeutic agent penetrates the deeper layers of the affected skin is cutaneous mycosis, such as athlete's foot, candidal vulvovaginitis, and other fungal infections of the integument. in the context, the invention may be used by preparing and administering an SFA-based composition comprising a suitable topically active antifungal agent, in particular an azole such as clotrimazole, ketoconazole, or miconazole; or an allylamine, such as terbinafine, naftifine, or butenafine.

In a further embodiment, the disease to be treated is acne, such as acne vulgaris or other forms of acneiform eruptions.

In this case, the active ingredient may, for example, be selected from retinoids, such as retinol, retinal, tretinoin, isotretinoin, alitretinoin, etretinate, acitretin, tazarotene, bexarotene and adapalene; antiinfective agents such as azithromycin, erythromycin, clindamycin, or minocycline; or spironolactone.

According to another embodiment, the invention is used in the treatment of actinic keratosis, which is a premalignant condition of the skin characterised by the presence of thick, scaly, or crusty patches. In this case, the active ingredient may be selected from NSAIDs such as diclofenac, ketoprofene and flurbiporofene, but also 5-fluorouracil and imiquimod.

Moreover, the invention is suitable for the treatment of viral infections of the skin, such as herpes simplex, herpes zoster, and varicella. For this indication, an antiviral compound is incorporated in the SFA-based composition, such as acyclovir, penciclovir, or docosanol.

In a further embodiment, the composition of the invention comprises a local anaesthetic agent such as benzocaine, butamben, dibucaine, lidocaine, oxybuprocaine, pramoxine, proparacaine, proxymetacaine, and tetracaine. Such composition may be used to relieve pain or itching caused by conditions such as sunburn or other minor burns, insect bites or stings, or in preparation of minor surgical procedures.

A large number of cutabeous diseases and conditions involve symptoms related to inflammatory responses, such as most forms of dermatitis, including atopic dermatitis, seborrhoeic dermatitis, allergic dermatitis, contact dermatis and the like, but also certain forms of pruritus, psoriasis, allergies, nummular eczema, xerotic eczema, lichen sclerosis, lichen planus, discoid lupus, chapped feet, lichen simplex chronicus, poison ivy reactions, alopecia areata, nummular eczema etc. Often these conditions require therapy or symptomatic control with topical corticosteroids, which can also be formulated and administered advantageously according to the invention. Suitable corticosteroid which may be incorprated in an SFA-based composition include amcinonide, betamethasone dipropionate, clobetasol propionate, desonide, desoximetasone, diflorasone diacetate, fluocinolone acetonide, fluocinonide, flurandrenolide, fluticasone propionate, halcinonide, halobetasol proprionate, hydrocortisone, hydrocortisone butyrate, hydrocortisone valerate, mometasone furoate, prednicarbate, and triamcinolone acetonide.

The invention is further illustrated by the following examples.

EXAMPLES

Example 1

Tacrolimus was dissolved in a liquid carrier comprising F6H8 and 3.8 wt.-% ethanol to obtain a clear solution having a tacrolimus concentration of 1 mg/mL.

Excised human skin was obtained from a breast reduction surgical centre. Skin samples were washed with isotonic sodium chloride solution. The subcutaneous adipose layers were removed. Circular pieces of 20 mm in diameter (3.14 cm$^2$) were punched out, supported by filter gauze, and mounted in FRANZ diffusion cells in such a way that the dermal side was in contact with the acceptor fluid (PBS pH 7.4), which was continuously stirred and kept at 32° C. Loss through evaporation was avoided by means of a glass lid.

On each skin sample (epidermal side), an amount of 20 µL of the tacrolimus solution was placed and spread out evenly. After a testing time of 30 min, 300 min, or 1,000 min, respectively, the remaining tacrolimus solution on the samples was collected and the skin samples were removed. From each specimen, three small punch biopsies of 6 mm diameter (0.2827 cm$^2$) were obtained and frozen. At −40° C., the punch biopsies were cryomicrotomised as follows:

1 slice of 10 µm thickness, corresponding to the stratum corneum 4 slices of 20 µm each, corresponding to the vital epidermis 5×5 slices of 40 µm each, corresponding to 5 layers of dermis All slices and the remaining stumps were extracted, and the amount of tacrolimus was determined by HPLC-MS. Moreover, the acceptor fluid and the fluid removed from the stratum corneum after each test were also analysed for tacrolimus. Each test was performed in triplicate, using skin from three different donors.

For comparison, a similar series of experiments using a commercial tacrolimus ointment (Protopic® 0.1%, Astellas Pharma, 20 mg per skin sample and FRANZ cell) was conducted.

Figure 1:
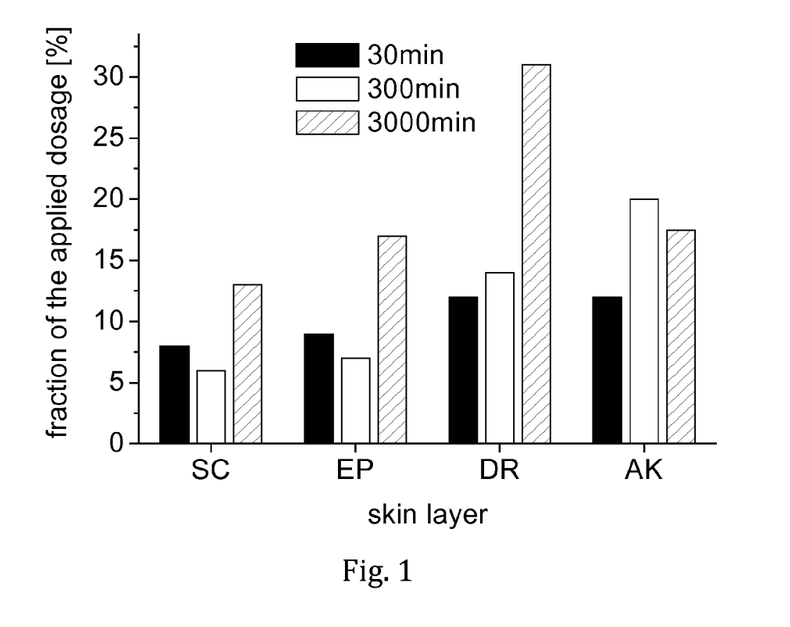
FIG. 1 shows the amount of tacrolimus found in different layers of the skin (SC=stratum corneum; EP=vital epidermis; DR=dermis; AK=hypodermis) 30 min, 300 min, and 1,000 min after administration as an SFA-based formulation to human skin, relative to the administered dose. For further details, see Example 1.
Figure 2:
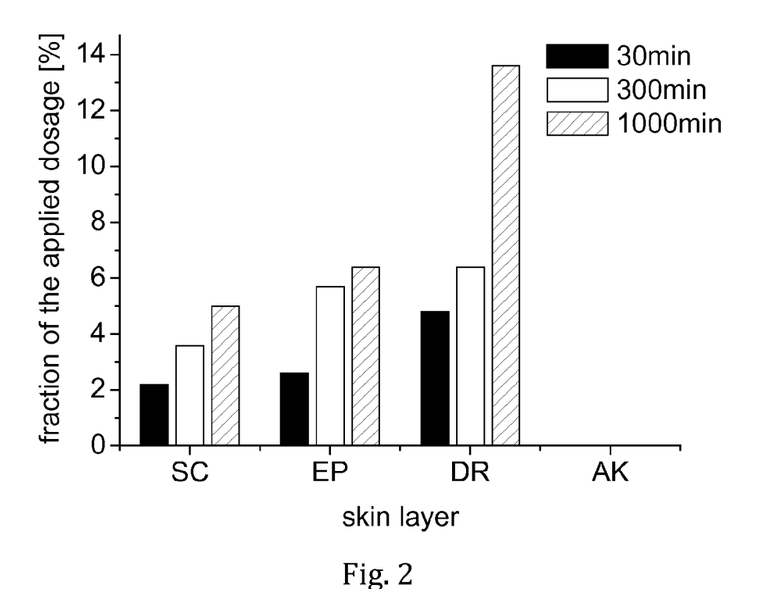
FIG. 2 shows the amount of tacrolimus found in different layers of the skin (SC=stratum corneum; EP=vital epidermis; DR=dermis; AK=hypodermis) 30 min, 300 min, and 1,000 min after administration of a commercial formulation (Protopic® 0.1%) to human skin, relative to the administered dose. For further details, see Example 1.
Figure 3:
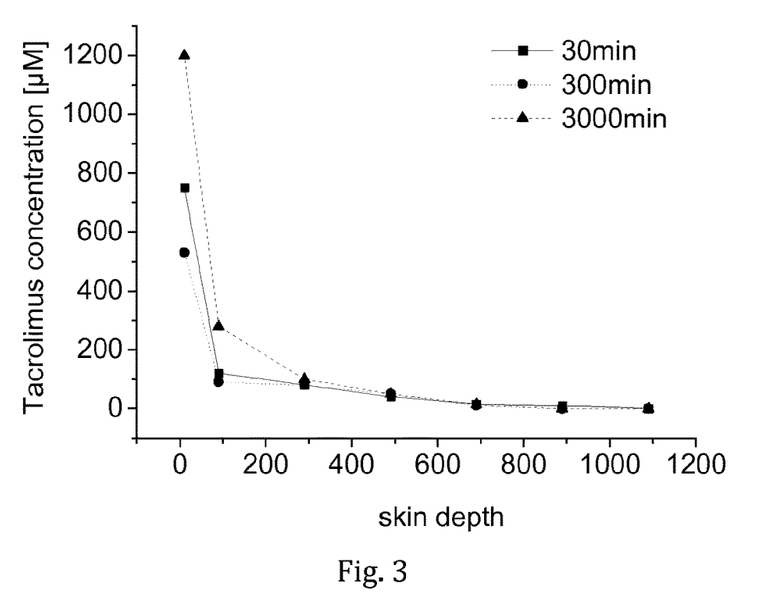
FIG. 3 shows the penetration profiles of tacrolimus 30 min, 300 min, and 1,000 min after administration as an SFA-based formulation to human skin, respectively. For further details, see Example 1.
Figure 4:
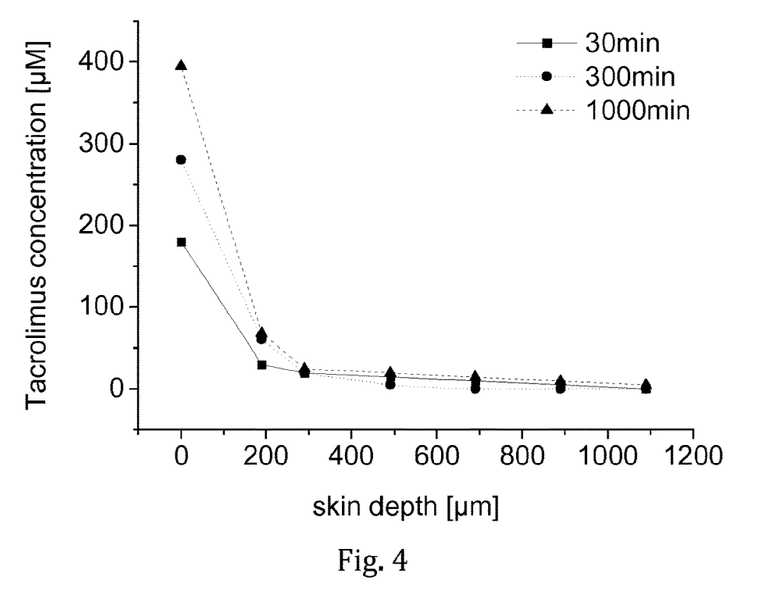
FIG. 4 shows the penetration profiles of tacrolimus 30 min, 300 min, and 1,000 min after administration a commercial formulation (Protopic® 0.1%) to human skin, respectively. For further details, see Example 1.

In result, it was found that the penetration of tacrolimus into the relevant skin layers was clearly superior in the case of the solution according to the invention. For example, already after 30 minutes approx. 9% of the administered dose was found in the vital epidermis, and approx. 12% was found in the layers of the dermis (see FIG. 1). For comparison, the commercial formulation delivered only about 2.5% of the dose to the vital epidermis and only about 5% to the dermis during the same period of time (see FIG. 2). After 1,000 minutes, the amount in the dermis was about 30% of the dose in the case of the solution of the invention (see FIG. 1), but only about 12.5% in the case of the commercial preparation (see FIG. 2). At all times, the penetration depth was much higher for the composition of the invention (see FIG. 3) than for the commercial product (see FIG. 4).

Example 2

A solution of radiolabeled D,L-α-tocopherol in F6H8 having a concentration of 10 mg/mL was prepared and used for a series of skin penetration experiments in analogy to Example 1, using excised human skin, with a few differences to the procedure of Example 1 as described below.

The amount of the formulation applied to each skin sample was 6 mg. The test period was 100 min. After the testing period, the stratum corneum of each sample was removed by the film stripping method (20 strips). Slices of the vital epidermis and the dermis were however obtained by microtomy at −40° C.

For comparison, three pharmacopoeial ointment formulations incorporating the same concentration of D,L-α-tocopherol were prepared and tested: "Unguentum emulsificans aquosum" (DAB), "Basiscreme" (DAC), and "Lanae alcoholum unguentum aquosum" (DAB).

Figure 5:
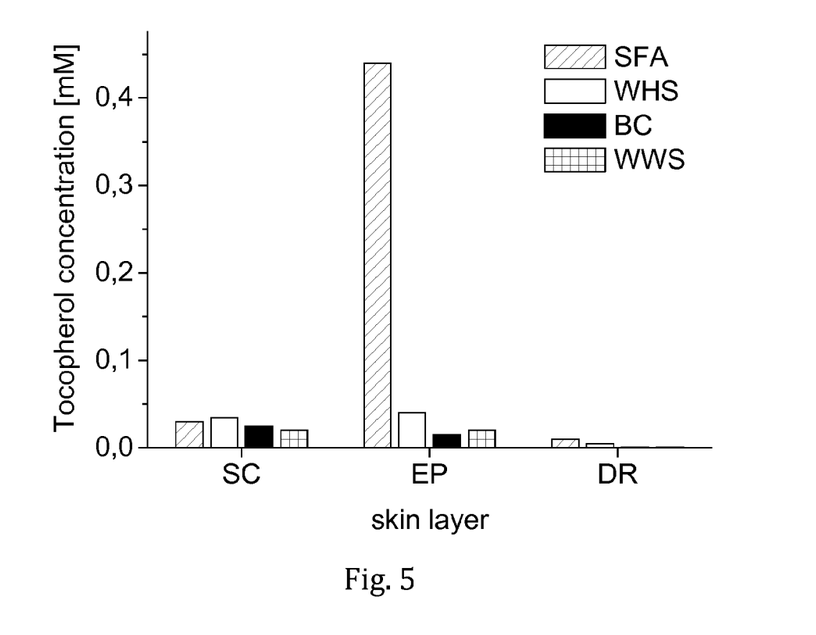
FIG. 5 shows the concentration of D,L-α-tocopherol found in different layers of the skin (SC=stratum corneum; EP=vital epidermis; DR=dermis) 100 min after administration as SFA-based formulation (SFA), Unguentum emulsificans aquosum DAB (WHS), Basiscreme DAC (BC), Lanae alcoholum unguentum aquosum DAB (WWS). For further details, see Example 2.

In result, it was surprising to find that the SFA-based formulation resulted in a much higher concentration of tocopherol in the vital epidermis than the three conventional formulations (see FIG. 5).

Example 3

The series of experiments of Example 2 were repeated in analogy, but using radiolabeled betamethasone-17,21-dipropionate as active ingredient at a concentration of 1 mg/mL instead of tocopherol. Another difference was that the SFA-based formulation of the drug contained 2.5 wt.-% ethanol.

Figure 6:
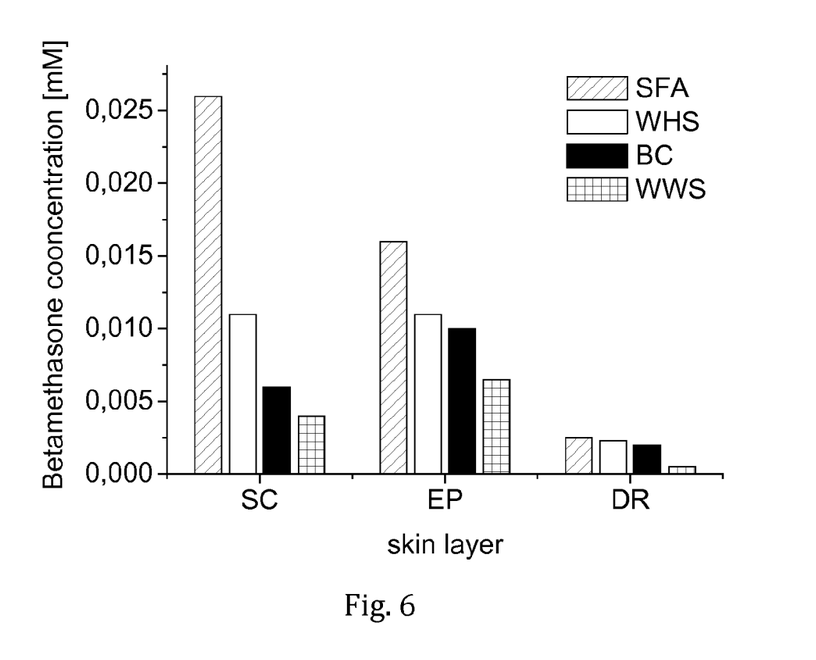
FIG. 6 shows the concentration of betamethasone-17,21-dipropionate in different layers of the skin (SC=stratum corneum; EP=vital epidermis; DR=dermis) 100 min after administration as SFA-based formulation (SFA), Unguentum emulsificans aquosum DAB (WHS), Basiscreme DAC (BC), Lanae alcoholum unguentum aquosum DAB (WWS). For further details, see Example 3.

Here it was found that the drug concentration in the skin layers was highest in the case of the SFA-based formulation of the invention, with a clear difference between the tested formulations with respect to the stratum corneum and the vital epidermis, but somewhat less differentiation in the dermis (see FIG. 6).

Example 4

An SFA-based microemulsion with tacrolimus was prepared. Basically, 10 mg of tacrolimus were dissolved in 1.5 mg of Tween® 80 and 2 g of Brij® 30. Then 2 g of 1,2-pentandiole were added, followed by 0.3 g of F6H8 and 0.7 g of isopropyl myristate. After gentle stirring, 4 g of water were added and the mixture was homogenised until it had a transparent appearance.

The invention claimed is:

1. A method for the prevention or treatment of a disease or condition affecting the skin, wherein the disease or condition affecting the skin is psoriasis, comprising administering to the skin a topical pharmaceutical composition comprising an effective amount of an active ingredient which is an immunosuppressant selected from tacrolimus, sirolimus, and ciclosporin A, and a semifluorinated alkane according to formula

RFRH wherein RF is a linear perfluorinated hydrocarbon segment with 4 to 12 carbon atoms, and RH is a linear alkyl group with 4 to 8 carbon atoms; wherein the semifluorinated alkane is selected from F4H5 and F6H8, wherein F means a perfluorinated hydrocarbon segment, H means a non-fluorinated segment, and the number is the number of carbon atoms of the respective segment;

and wherein the composition is in the form of a liquid solution; and wherein the composition comprises a physiologically acceptable cosolvent selected from ethanol, isopropyl alcohol, glycerol, and propylene glycol.

2. The method of claim 1, wherein the semifluorinated alkane is F6H8.

3. The method of claim 1, wherein the composition is in the form of a single-phase liquid solution.

4. The method of claim 1, wherein the semifluorinated alkane is F4H5.

5. The method of claim 1, wherein the disease or condition affects the vital epidermis, dermis, and/or hypodermis of the skin.

6. The method of claim 1, wherein the active ingredient is delivered to the vital layers below the stratum corneum of the epidermis.

7. The method of claim 1, wherein the method is for the prevention or treatment of skin affected by psoriasis, and wherein the topical pharmaceutical composition is administered to the skin.

8. The method of claim 1, wherein the immunosuppressant is tacrolimus.

9. The method of claim 4, wherein the physiologically acceptable cosolvent is selected from ethanol and isopropyl alcohol.

10. The method of claim 2, wherein the immunosuppressant is tacrolimus.

11. The method of claim 1, wherein the physiologically acceptable co-solvent is selected from ethanol and isopropyl alcohol.

12. The method of claim 2, wherein the physiologically acceptable co-solvent is selected from ethanol and isopropyl alcohol.

13. The method of claim 10, wherein the physiologically acceptable co-solvent is selected from ethanol and isopropyl alcohol.

14. The method of claim 1, wherein the physiologically acceptable co-solvent is ethanol.

15. The method of claim 2, wherein the physiologically acceptable co-solvent is ethanol.

16. The method of claim 10, wherein the physiologically acceptable co-solvent is ethanol.

17. The method of claim 14, wherein the ethanol is present at a concentration of up to 5 wt %.

18. The method of claim 15, wherein the ethanol is present at a concentration of up to 5 wt %.

19. The method of claim 16, wherein the ethanol is present at a concentration of up to 5 wt %.

\* \* \* \* \*